United States Patent [19]

Rosen et al.

[11] Patent Number: 5,541,522

[45] Date of Patent: Jul. 30, 1996

[54] CONFORMAL TIP FOR COAXIAL TEST PROBE FOR NON-DESTRUCTIVE TESTING OF DIELECTRIC/MAGNETIC MATERIALS

[75] Inventors: Mark D. A. Rosen, Woodbridge, Conn.; Paul J. Scheno, Bay Port; Mark A. Lizza, Oyster Bay, both of N.Y.

[73] Assignee: Northrop Grumman Corporation, Los Angeles, Calif.

[21] Appl. No.: 349,811

[22] Filed: Dec. 6, 1994

[51] Int. Cl.$^6$ .......................... G01R 27/04; G01R 27/32; G01R 31/02; G01R 27/72
[52] U.S. Cl. .......................... 324/642; 324/226; 324/262; 324/761
[58] Field of Search ...................... 324/228, 226, 324/262, 642, 761, 637, 645, 715, 727, 718, 719

[56] References Cited

U.S. PATENT DOCUMENTS

| | | | |
|---|---|---|---|
| 2,722,636 | 11/1956 | Minchom | 324/216 |
| 4,061,969 | 12/1977 | Dean | 324/761 |
| 4,740,746 | 4/1988 | Pollock et al. | 324/761 |
| 5,389,875 | 2/1995 | Rosen et al. | 324/228 |

OTHER PUBLICATIONS

Baker-Jarvis, et al., "Analysis of an Open-Ended Coaxial Probe with Lift-Off for Nondestructive Testing," *IEEE Transactions on Instrumentation and Measurement* 43(5): 711–718.

Misra (1987), "A Quasi-Static Analysis of Open-Ended Coaxial Lines," *IEEE Transactions on Microwave Theory and Techniques* 35(10): 925–928.

Misra (1987), "A Study on Coaxial Line Excited Monopole Probes for In Situ Permittivity Measurements," *IEEE Transactions on Instrumentation and Measurement* 36(4): 1015–101.

Xu et al. (1991), "Some calculation methods and universal diagrams for measurement of dielectric constants using open-ended coaxial probes", *IEE Proceedings–H* 138(4): 356–360.

Zheng et al. (1991), "Permittivity Measurements Using a Short Open-Ended Coaxial Line Probe", *IEEE Microwave and Guided Wave Letters* 1(11): 337–339.

Zheng et al. (1992), "Theoretical and Experimental Study of Measurement of Microwave Permittivity Using Open Ended Elliptical Coaxial Probes," *IEEE Transactions on Microwave Theory and Techniques* 40(1): 143–150.

*Primary Examiner*—Walter E. Snow
*Attorney, Agent, or Firm*—Terry J. Anderson; Karl J. Hoch, Jr.

[57] ABSTRACT

A conformal tip for an open-end coaxial sensor utilized for non-destructive testing of material, includes a first plurality of resiliently retractable pins connected axially with a first conductor of the coaxial sensor and a second plurality of resiliently retractable pins connected axially with a second conductor of the coaxial sensor.

19 Claims, 3 Drawing Sheets

5,541,522

1

CONFORMAL TIP FOR COAXIAL TEST PROBE FOR NON-DESTRUCTIVE TESTING OF DIELECTRIC/MAGNETIC MATERIALS

BACKGROUND OF THE INVENTION

1. Field of the Invention

The present invention relates generally to non-destructive test apparatuses that includes a probe for evaluating the intrinsic electromagnetic properties of a dielectric/magnetic structure, and more particularly to an improved open-ended transmission line probe having a conformal tip.

2. Description of the Prior Art

In many scientific and testing endeavors it is valuable to non-destructively test a solid material's electromagnetic properties, such as permittivity "$\epsilon$" and magnetic permeability "$\mu$". A particularly useful apparatus for evaluating the magnetic character of materials is the device disclosed in patent application U.S. Ser. No. 034,344, entitled "Apparatus for Nondestructive Testing of Dielectric/Magnetic Materials" that is assigned to the same assignee of the instant invention, and the disclosure of which is incorporated by reference herein. In a preferred embodiment disclosed in this reference, the apparatus for non-destructive testing of dielectric/magnetic materials includes a probe structure comprising a coaxial cable sensor and a current carrying coil for applying a carefully controlled magnetic field to the solid material being tested. Soft magnetic sleeves surrounding the coaxial cable sensor function to concentrate the applied magnetic field in the specific area of the material to be tested. The coaxial cable sensor functions to transmit an electromagnetic wave into and couple the reflected wave from the sample to a measuring device, such as a network analyzer, so that properties of the material may be quantitatively or qualitatively deduced. Since the surface of solid samples must be flat and polished in order to make accurate and reproducible measurements, these type of sensors have been limited to the laboratory where such stringent conditions could easily be met. In the real world, however, surfaces might not only be rough, but curved.

It is the case that other open-ended coaxial sensors in nondestructive testing (NDT) have been severely limited due to the stringent requirements for the surface finish of the solid materials to be measured. For instance, it is desirable that the coaxial sensor's open end make perfect contact with the surface to ensure that an electromagnetic wave will propagate (fringe) into the material and not be partially reflected due to any air gaps that may be present. Usually this has required that the surface of materials be lapped and polished or that they be soft enough to conform to the probe's open end. This has limited value in the real world where surfaces may not only be rough, but curved.

SUMMARY OF THE INVENTION

It is therefor an object of the instant invention to provide a coaxial test probe sensor for non-destructive testing that has a conformal tip comprising a plurality of individually spring loaded pins axially connected with the outer circumference of an inner conductor of the coaxial sensor and a plurality of individually spring loaded pins axially connected with the inner surface of an outer conductor of the coaxial sensor that can be individually compressed to conform to materials having rough and curved surfaces.

Still another object of the instant invention is to provide a coaxial test probe sensor for non-destructive testing that has a conformal tip comprising a plurality of individual pins as described above, such that, when used in non-destructive testing of magnetic and dielectric properties of materials, the pins of the probe will maximally contact the tested material's surface and not interrupt any surface current flow when making measurements.

It is yet another object of the instant invention to provide a coaxial test probe sensor for non-destructive testing that has a conformal tip comprising a plurality of individual pins as described above wherein the pins and corresponding springs are formed of magnetic or non-magnetic material.

These and other objects of the invention are achieved with a conformal tip for an open-end coaxial sensor utilized for non-destructive testing of material, includes a first plurality of resiliently retractable pins connected axially with a first conductor of the coaxial sensor and a second plurality of resiliently retractable pins connected axially with a second conductor of the coaxial sensor. Each of the plurality of pins are individually spring loaded and compressible to enable the coaxial sensor to maximally conform with a rough or curved material surface when contacting the surface.

DETAILED DESCRIPTION OF THE INVENTION

Figure 1:
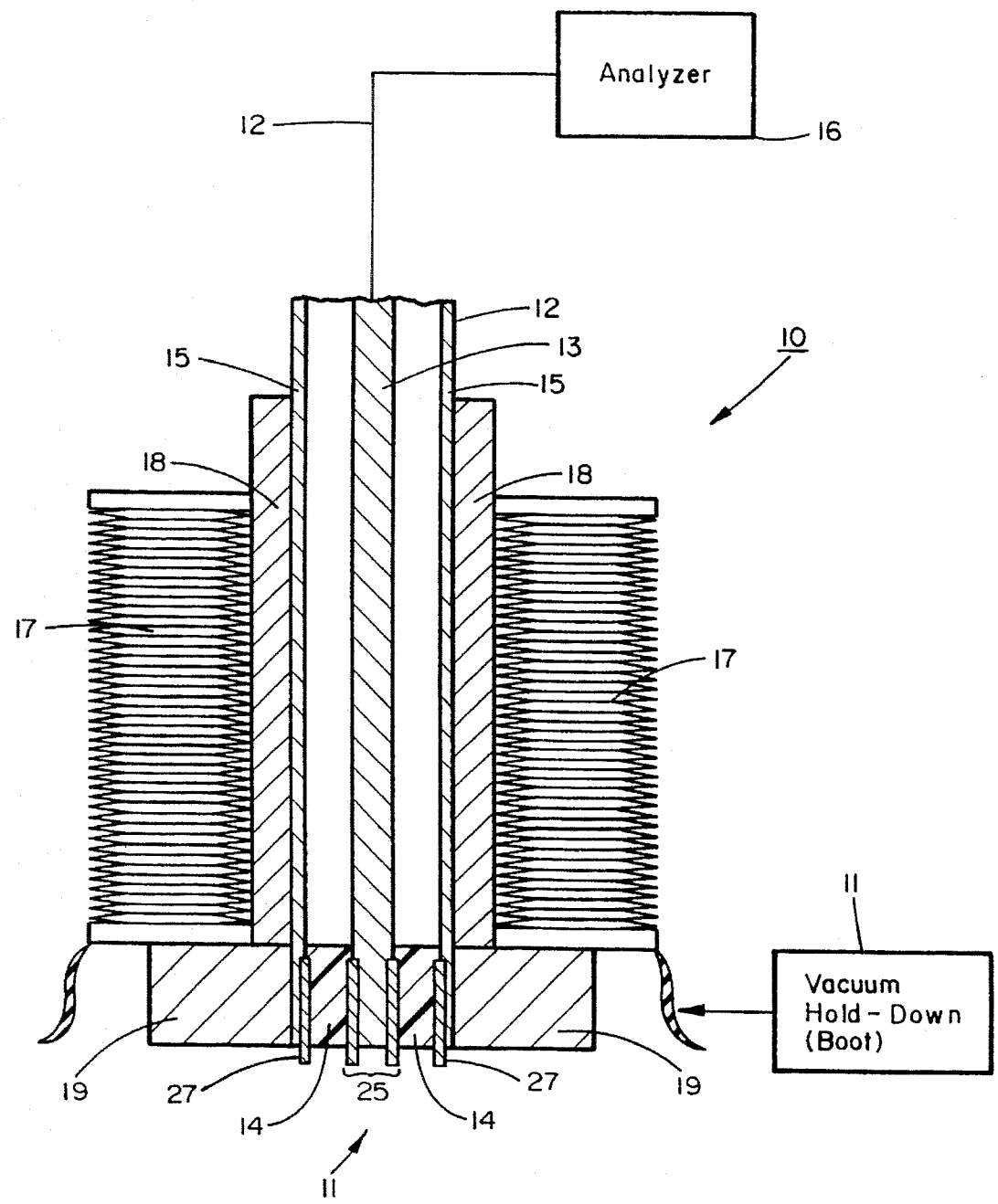
FIG. 1 is a cross-sectional diagram of the open-ended coaxial probe 10 having a conformal tip 11 of the instant invention.

FIG. 1 illustrates an open-end coaxial (transmission line) probe 10 implementing the conformal tip 11 of the invention. As described in abovementioned patent application U.S. Ser. No. 034,344, the probe includes a coaxial cable 12 which includes an inner conductor 13 surrounded, respectively by a spacer 14 made of dielectric material such as TEFLON®, and by an outer conductive member 15. The function of the coaxial cable 12 in this type of probe is to simply guide electromagnetic radiation towards the material, and to guide reflected waves away from the material to an analyzer such as network analyzer 16 depicted schematically in FIG. 1.

Figure 2A:
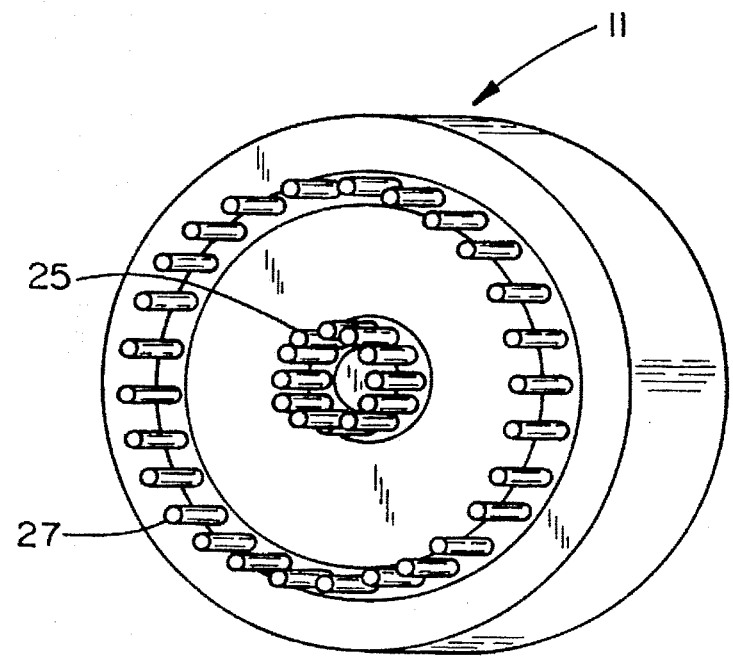
FIG. 2(a) is a photograph depicting an open-ended coaxial sensor of the instant invention having a conformal tip of a first diameter.
Figure 2B:
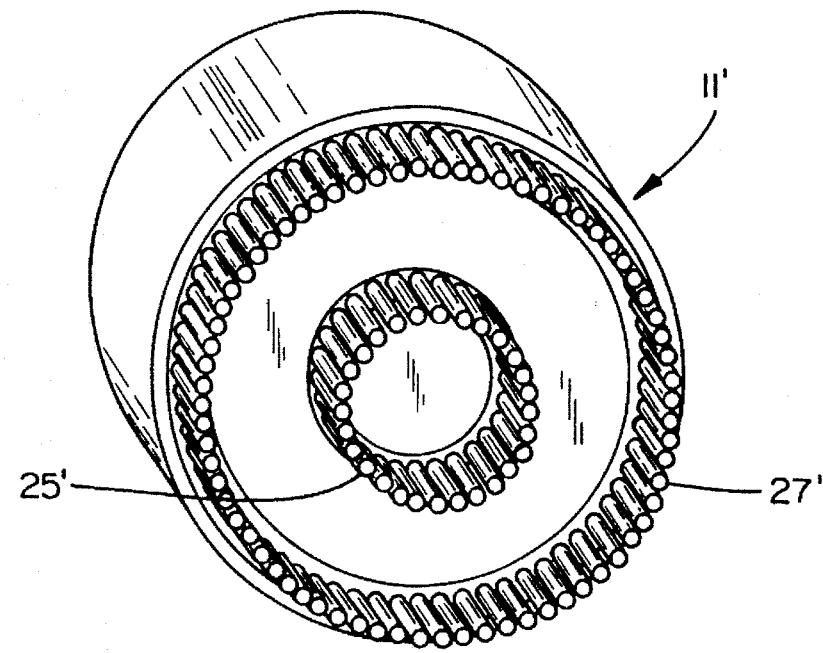
FIG. 2(b) is a photograph depicting an open-ended coaxial sensor having a conformal tip of a second diameter.

FIGS. 1 and 2(a) illustrate the conformal tip 11 of the instant invention having a first diameter of about 7.0 mm (not to scale). A second conformal tip 11' is shown in FIG. 2(b) having a second diameter of about 14 mm. Each probe 11, 11' contains a first set of pins 25, 25' (respectively) axially aligned with and connecting the inner conductor 13 of the coaxial probe, and, a second set of pins 27, 27' (respectively) that are axially aligned with and connecting the outer conductor 15 of the coaxial probe. As will be explained in further detail below, each of the plurality of pins 25, 27 comprises a biasing spring and plunger combination within a pin housing, the spring and housing combination enabling resilient retractable movement of the plunger within the housing such that the plunger tip will easily conform to any material surface, whether rough or curved. The pins 25, 27 will thus conform to a material surface creating good electrical contact without discontinuities or gaps so that the coaxial cable surface and axial current flow will allow an electromagnetic wave to propagate to the material's surface.

Figure 5:
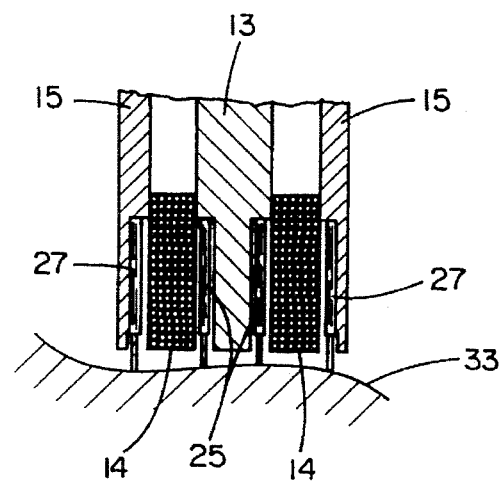
FIG. 5 is a detailed cross-sectional diagram of a conformal tip 11.

In order to ensure reproducibility of the test results using the probe 10, the inner and outer conductors 13, 15 must be held in secure contact with the material being tested. Fortunately, the unique features of the conformal tip 11 of the instant invention permits the open-end coaxial probe to more positively conform to any curve or rough surface of the material being tested. Specifically, as shown in FIGS. 3–5, and explained in further detail below, the plurality of individually spring loaded pins 25 and 27 function to maintain conforming contact with the surface 33 of any material to be tested, and, depending upon the materials of the pins, functions to further concentrate magnetic flux to the inner and outer conductors 13, 15, respectively when an external magnetic field is applied in the described below.

Each of the sets of pins 25, 27, (or, 25', 27') are custom manufactured and can be magnetic or non-magnetic depending upon a particular application. For instance, when measuring magnetic properties of a sample material as described above, it is desirable that pins 25, 27 and their associated springs be magnetic since this will optimize the magnetic field concentration that is needed for the probe to work when the permeability of magnetic materials is to be measured. Typical pins comprise magnetic material made of stainless steel, cobalt, nickel, iron, or alloys thereof. For other applications, the pins and springs may be of a nonmagnetic material such as beryllium copper.

Figure 3:
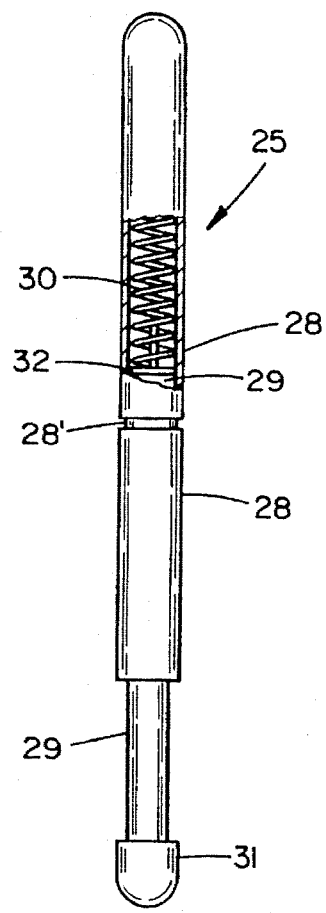
FIG. 3 is a detailed cross-sectional diagram of a pin 25 utilized in the conformal tip of the invention.
Figure 4:
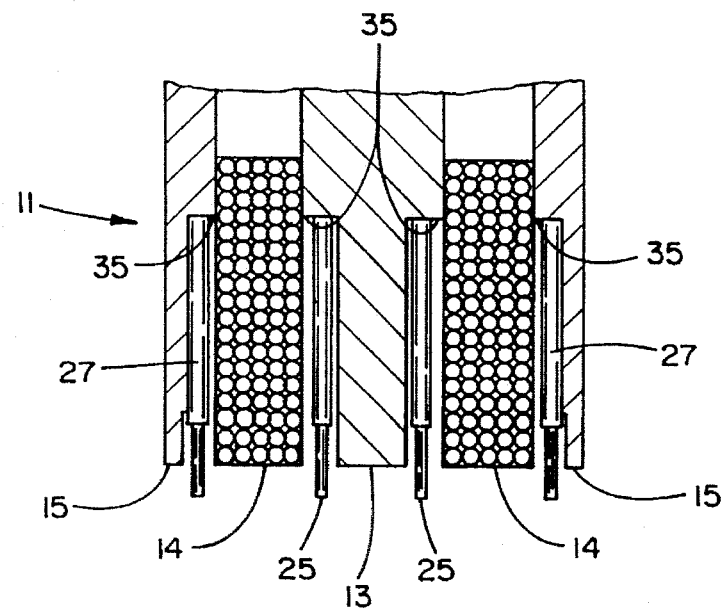
FIG. 4 is a detailed cross-sectional diagram of a conformal tip 11.

As shown in the preferred embodiment of FIG. 3, the barrel 28 of each pin 25 houses a plunger 29 having a biasing portion 32 that is operatively connected with spring 30 which may comprise gold plated beryllium copper or any other suitable non-magnetic material known to those skilled in the art. The plunger 29 and spring 30 may also be of a magnetic material such as alloys of nickel, cobalt, or even iron. The opposite end of the plunger 29 includes a tip portion 31 that extends outside the barrel for contacting a material surface. Preferably, the barrel of each pin 25 is about 27 mils in diameter and the length of the barrel and plunger is about 0.5 inches. Barrel 28 includes a notch 28' that acts in conjunction with a plunger stop (not shown) to define a fully extended position for the plunger. The plunger 29 may include a lip or flange to function as the plunger 29 stop. In another embodiment, the notch 28' may facilitate the connection of the pin housing within a conductor. It should be understood that pins of varying designs may be incorporated in the conformal tip of the invention. For instance, pins may include springs having one end soldered to the biasing portion of the plunger and the other end soldered to the barrel housing.

When a force is applied to the probe 10 to secure contact with a material surface, the plungers 29 of each contacting pin and their corresponding springs 30 are retracted within the barrel 28 from their fully extended position. To facilitate resilient retractibility of the plunger within the barrel housing, the spring constant of spring 30 is preferably low, on the order of 0.22 oz. at preload, and 0.95 oz. when compressed to ⅔ of its maximum stroke. It is understood that the material of the spring 30 must be chosen to ensure a low spring tension, and may vary in accordance with the particular material to be tested. In the preferred embodiment, the maximum stroke of the pin is about 0.1 inches. For certain applications, however, pins may be designed with strokes of up to 0.25 inches to allow a greater flexibility when conforming with materials having largely varying surfaces profiles. It should be mentioned that when probes 10 having conformal tips 11 of the invention contact the material to be tested, optimum test results occur when the individual pins are compressed to their fullest extent possible in accordance with the material's surface. Thus, even though all pins may be compressed at different lengths (see FIG. 5) depending upon the tested material's surface contour, they should be compressed to their fullest extent to ensure uniformity of test results.

The pin tip portion 31 may vary in accordance with the application, but the curved "radius" tip, as shown in FIG. 3, is preferred. The degree of curvature of the radius tip may be varied depending upon the diameter of the pin utilized. Other tips may be flat, beveled, crowned, or pointed, but the radius tip, it is found, best ensures the safety and integrity of most material surfaces to be non-destructively tested, and ensures reliable test measurements.

The conformal tip as shown in the detail cross-sectional view of FIG. 4, is manufactured precisely under controlled conditions. As shown in FIG. 4, a lip or cutout 35 is created in the outer circumference of the inner conductor 13 and the inner circumference of the outer conductor 15 for accommodating connection with the pins 25 and 27. A low temperature conducting solder, such as a gallium-indium eutectic, or the like, is used to connect each pin barrel to the lip or cutout portion in the conductors. This is done in such a manner as to ensure that good electrical continuity exists between the pins and the conductors. Otherwise, poor electrical continuity may tend to affect and alter test measurements. It should be mentioned that the maximum number of pins 25,27 is chosen to ensure maximum conductivity with the material to be tested and the inner and outer coaxial conductors, respectively. For instance, the conformal tip of FIG. 2(b) contains an inner conductor having twenty-five (25) pins 25 and an outer conductor having sixty-seven (67) pins. In another embodiment, it is possible to create individual cutout or shelf portions in the inner and outer conductors to accommodate a corresponding pin means.

The probe 10 may additionally include a coil 17 which serves to apply a magnetic field to the material being tested, and additionally includes structures for concentrating that field in a controllable manner. The coil 17 is a conventional electromagnetic coil connected to a current source in order to produce a field in the material. Flux concentration initially is provided by a soft magnetic sleeve 18 of generally cylindrical shape placed between the outer conductor 15 of the cable and the coil 17, the sleeve including a nonmagnetic flange 19 which supports the coil 17 and may provide a contact surface for the material. The flux concentration is further abetted by the use of a soft magnetic member or rod 13 as the inner conductor of the coaxial cable. Because the sleeve is spaced from the structure being analyzed by flange 19, while pins 25 of inner conductor 13 contact the material, flux from sleeve 18 will tend to concentrate at the pins 25 of inner conductor 13, ensuring that the flux is directed to the location needed, which is at the point where the transmitted electromagnetic wave penetrates the material.

Modifications to the probe 10 having the conformal tip of the instant invention include the use of a flexible material for flange 19 which may be either conducting or coated with a metallic layer, to allow the probe to better conform to curved materials. Also, a flexible boot and vacuum system depicted schematically by box 11 in FIG. 1, may optionally be fitted around flange 19 in order to draw the probe more firmly against the material being tested. As a result, it is contemplated that a thin protective coating on the probe face to protect both the probe and the part being tested may be required.

The open-end coaxial (transmission line) probe 10 of FIG. 1, and the conformal tip 11 thereof, facilitates a simple test method which involves turning a magnetic field on and off and measuring the magnitude and phase of the reflected wave under both conditions. This method can be expanded to obtain a depth profile of the structure, utilizing the properties of dependence of the penetration of the electromagnetic wave on frequency and on the size of the probe. By varying these parameters, different depths of a coating can be evaluated and a profile made. It should be understood that the size of the coax tip 11 determines the spatial region sampled, the depth and volume of the material sampled and the maximum operating frequency of the device. Thus, the probe shown in FIG. 2(a) may be used when supplying electromagnetic waves at frequencies up to 18 GHz and preferably 12 GHz, while the probe having the larger diameter tip as shown in FIG. 2(b) may be used when supplying electromagnetic waves at frequencies up to 8 GHz and preferably 5-6 GHz.

As a result of the coil 17, flux concentrating members 13 and 18, and the pins 25, 27 of respective inner and outer conductors, the magnetic character of a material can be analyzed by altering this characteristic of the material in a controlled way through application of an external field in order to prevent the material's magnetic spins or domains from moving and interacting with the electromagnetic field vectors of the incident wave. Even when the vector interactions cannot be controlled precisely enough to make a quantitative measurement of the intrinsic permeability or permittivity, the information obtained by turning on and off the field can be used in a qualitative way where comparisons to a set of standards can be made.

An exemplary probe 10 having the conformal tip of FIG. 2(a) includes a precision 7 mm. coaxial line surrounded by an electromagnetic coil 17 containing 1820 turns, the coil generating a 2.2 KG field at the conformal tip upon connection to a current of 1 ampere. The materials of the flux concentrators in this example are, respectively, 1006 stainless steel for the sleeve and pure iron for the center conductor rod.

Although shown and described in what we believe to be the most practical and preferred embodiments, it is apparent that departures from the specific methods and designs described and shown will suggest themselves to those skilled in the art and may be made without departing from the spirit and scope of the invention. We, therefore, do not wish to restrict ourselves to the particular constructions described and illustrated, but desire to avail ourselves of all modifications that may fall within the scope of the appended claims.

What is claimed is:

1. A conformal tip for an open-end coaxial sensor utilized for non-destructive testing of material, said coaxial sensor having first and second conductors, said tip comprising:

a first plurality of individually resiliently retractable pin means connected axially with said first conductor of said coaxial sensor;

a second plurality of individually resiliently retractable pin means connected axially with said second conductor of said coaxial sensor;

each of said first conductor and said second conductor including a cutout portion, each of said first and second plurality of pin means being secured axially to said respective first and second conductors within said respective cutout portions.

2. The conformal tip for an open-end coaxial sensor as claimed in claim 1, wherein each of said resiliently retractable pin means comprises:

a) a pin housing;

b) a plunger means having a biasing portion within said tip housing and a tip portion extending outside said housing;

c) a spring means operatively connected with said biasing portion of said plunger enabling retractable movement of said plunger means within said pin housing.

3. The conformal tip for an open-end coaxial sensor as claimed in claim 2, wherein said tip portion defines a curved shape of a predetermined radius.

4. The conformal tip for an open-end coaxial sensor as claimed in claim 2, wherein said spring means has a spring constant of predetermined value.

5. The conformal tip for an open-end coaxial sensor as claimed in claim 4 wherein said spring constant ranges anywhere from 0.2 ounces to 1.0 ounces.

6. The conformal tip for an open-end coaxial sensor as claimed in claim 1, wherein each said first and second plurality of resiliently retractable pin means comprise non-magnetic material.

7. The conformal tip for an open-end coaxial sensor as claimed in claim 1, wherein each said first and second plurality of resiliently retractable pin means comprise magnetic material.

8. The conformal tip for an open-end coaxial sensor as claimed in claim 6, wherein said non-magnetic material includes beryllium copper or an alloy thereof.

9. The conformal tip for an open-end coaxial sensor as claimed in claim 7 wherein said magnetic material includes cobalt, nickel, iron, or alloys thereof.

10. A non-destructive test apparatus, comprising:

coaxial cable sensor having inner and outer conductors for directing an electromagnetic wave at a material to cause the wave to reflect from the material and for receiving the reflection of the wave;

an electromagnetic wave analyzer coupled to one end of said sensor; and a conformal tip coupled to an opposite end of said sensor, said conformal tip having a first plurality of individually resiliently retractable pin means connected axially with said inner conductor of said coaxial cable sensor, and a second plurality of individually resiliently retractable pin means connected axially with said outer conductor of said coaxial cable sensor;

each of said inner conductor and said outer conductor including a cutout portion, each of said first and second plurality of pin means being secured axially to said respective first and second conductors within said respective cutout portions.

11. The non-destructive test apparatus according to claim 10 further including means for selectively applying a magnetic field to the material simultaneously with the reflection of the electromagnetic wave from the material.

12. The non-destructive test apparatus according to claim 11, wherein said magnetic field applying means comprises a coil wrapped around said second conductor of said cable, said magnetic field applying means further comprises means for concentrating magnetic flux on said material.

13. The non-destructive test apparatus according to claim 12, wherein said flux concentrating means comprises a soft magnetic sleeve surrounding said second conductor and in turn surrounded by said coil.

14. The non-destructive test apparatus according to claim 10, wherein each said first and second plurality of resiliently retractable pin means of said conformal tip comprise magnetic material.

15. The non-destructive test apparatus according to claim 10, wherein each said first and second plurality of resiliently retractable pin means of said conformal tip comprise non-magnetic material.

16. The non-destructive test apparatus according to claim 14, wherein said magnetic material includes cobalt, nickel, iron, or alloys thereof.

17. The non-destructive test apparatus according to claim 10, wherein each of said resiliently retractable pin means comprises:

a) a pin housing;

b) a plunger means having a biasing portion within said housing and a tip portion extending outside said housing;

c) a spring means operatively connected with said biasing portion of said plunger enabling retractable movement of said plunger means within said pin housing.

18. The non-destructive test apparatus according to claim 17, further comprising flange means for holding said apparatus against said material, said means including a flexible boot attached to the apparatus and placed against the material, and means for evacuating the boot.

19. The non-destructive test apparatus according to claim 18 wherein said flange means is flexible to easily conform with a material surface.

* * * * *